United States Patent
Herzen et al.

(10) Patent No.: US 7,066,023 B2
(45) Date of Patent: Jun. 27, 2006

(54) DISTRIBUTED SENSOR ARRAY FOR FLUID CONTAMINANT MONITORING

(75) Inventors: Brian Von Herzen, Carson City, NV (US); Glenn R. Rink, Paradise Valley, AZ (US)

(73) Assignee: Environmental Security Corporation, Scottsdale, AZ (US)

( * ) Notice: Subject to any disclaimer, the term of this patent is extended or adjusted under 35 U.S.C. 154(b) by 260 days.

(21) Appl. No.: 10/892,516

(22) Filed: Jul. 14, 2004

(65) Prior Publication Data

US 2005/0120778 A1 Jun. 9, 2005

Related U.S. Application Data

(60) Provisional application No. 60/487,274, filed on Jul. 14, 2003.

(51) Int. Cl.
*G01F 23/00* (2006.01)
*G01N 33/00* (2006.01)

(52) U.S. Cl. .................. 73/304 R; 73/61.41
(58) Field of Classification Search ............ 73/304 R, 73/290 R
See application file for complete search history.

(56) References Cited

U.S. PATENT DOCUMENTS

| 3,762,214 | A | * | 10/1973 | Bogusz ................... 73/61.41 |
| 3,980,881 | A | | 9/1976 | Veach et al. ............ 250/261 |
| 3,987,457 | A | | 10/1976 | Moore .................... 343/840 |
| 4,977,619 | A | | 12/1990 | Crimmins ................ 398/96 |
| 5,545,982 | A | | 8/1996 | Vlakancic ................ 324/174 |
| 5,646,863 | A | | 7/1997 | Morton ................... 702/23 |
| 5,728,943 | A | | 3/1998 | Colter, Jr. et al. ......... 73/799 |
| 5,821,405 | A | | 10/1998 | Dickey et al. ............ 73/53.01 |
| 6,091,979 | A | | 7/2000 | Madsen ................... 600/377 |
| 6,444,172 | B1 | | 9/2002 | Fukunaga et al. ......... 422/68.1 |
| 6,535,822 | B1 | | 3/2003 | Mansky et al. ............ 702/21 |
| 2002/0089896 | A1 | | 7/2002 | Behrens et al. ............ 367/154 |
| 2003/0090200 | A1 | | 5/2003 | Topelberg et al. ......... 313/511 |

FOREIGN PATENT DOCUMENTS

| WO | WO 00/51360 | 8/2000 |
| WO | WO 02/41095 | 5/2002 |

OTHER PUBLICATIONS

"CO.L.MAR: Vertical Array," web page printed Jun. 2003 from http://www.colmaritalia.it/net/towed_e.html.
"CO.L.MAR: Cetacean Array," web page printed Jun. 2003 from http://www.colmaritalia.it/net/array_e.html.

* cited by examiner

*Primary Examiner*—Hezron Williams
*Assistant Examiner*—Tamiko Bellamy
(74) *Attorney, Agent, or Firm*—Louis J. Hoffman; Edwin A. Suominen (57) ABSTRACT

A disclosed fluid purity monitoring system employs a network of preferably information-transmissive cables fixed in place within a body of fluid. Sensors sensitive to fluid impurities are supported at various places on the network. Data representative of impurity levels transmits to a collection point via the same cables at which the sensors are supported. One system employs at least two pluralities of sensors sensitive to different fluid impurities. Another system employs electrically conductive cables fixed in place substantially in a common plane, with some cables oriented substantially parallel to each other and intersecting other cables. In that system, the data transmits to the collection point via a separate electrical circuit for each one of the sensors. Each circuit includes a series connection of the pair of cables that intersect proximate to the sensor's support point on the network. Advantageous variations and methods are also disclosed.

47 Claims, 6 Drawing Sheets

DISTRIBUTED SENSOR ARRAY FOR FLUID CONTAMINANT MONITORING

CROSS REFERENCE TO RELATED APPLICATIONS

This application claims the benefit of, and incorporates herein by reference, U.S. provisional application Ser. No. 60/487,274 filed Jul. 14, 2003.

BACKGROUND OF THE INVENTION

Since the terrorist attacks on the United States in September 2001, a new awareness has arisen about vulnerability of drinking reservoirs to radiological, chemical, and biological threats from terrorists. The U.S. Homeland Security Department has mandated that defensive measures be taken to protect the nation's water supplies from terrorist attack. Yet few systems are available today that provide cost effective early-detection and response systems for warning of attacks on our water supplies. Existing approaches using periodic sampling do not suffice to protect the civilian population from water supply contamination, leaving municipalities with few safety choices and limited options for complying with the Homeland Security mandate.

In the western U.S., for example, water resources are becoming increasingly precious, as demands on water utilization increase. This trend may well make the western water supplies of the U.S. especially vulnerable to terrorist attack that could simultaneously affect many of the cities of the southwest. The need to protect those valuable resources is especially acute.

In addition to the limited availability of reservoir protection systems, a fundamental problem is that, even if such systems were available, the government is hard pressed to defend against the myriad of biological, chemical and radiological threats that terrorist organizations have at their disposal today. Once an attack occurs on a single municipality with some unexpected agent, the demand for detectors of that agent can be expected to skyrocket. The market needs a rapid response system that can quickly provide sensors customized for the latest threat once it is identified. That requirement places an enormous burden on the manufacturing capacity of those sensors. A strategy is needed to prepare for the expected surge in demand after a terrorist event. A solution for these problems must be versatile and flexible, capable of responding in time to emergency situations. What is needed is an early warning system that can provide a real-time response, to prevent water resource disasters.

SUMMARY OF THE INVENTION

Fluid purity monitoring systems and methods according to various aspects of the invention employ a network of information-transmissive cables in place within a body of fluid. Sensors sensitive to fluid impurities are supported at various places on the cable network. According to a particular aspect, data representative of fluid impurity levels is transmitted to a collection point via the same cables that make up the cable network at which the sensors are supported.

Systems and methods according to another aspect of the invention support at least two pluralities of sensors, which are sensitive to different fluid impurities. The data transmitted to the collection point is representative of the level of the different fluid impurities. According to particular aspects of the invention, a new set of sensors responsive to different types of fluid impurities can be added or used in place of a previously placed type of sensor.

Systems and methods according to another aspect of the invention employ electrically conductive cables that are fixed in place within the fluid substantially in a common plane. Some cables of the network are oriented substantially parallel to each other and intersect other cables of the network. The systems and methods support the plurality of sensors on the network proximate to different junctions of pairs of the cables. The data representative of the degree of fluid impurities in the fluid transmits to the collection point via a separate electrical circuit for each one of the sensors. The electrical circuit for each sensor includes a series connection of the pair of cables that intersect proximate to where the sensor is supported on the network. In other words, a given flow of current moves toward the intersection through one cable of the pair and away from the intersection through the other cable.

In systems and methods according to various particular aspects of the invention, the electrical signals can be modulated for multiple signal access to a shared transmission cable, e.g., with CDMA and different spreading codes. The sensors can be housed within sensor modules, which can receive analog data proportional to a level of fluid impurity from their respective sensors and transmit modulated digital data based on the analog data from the sensor module to the collection point. The sensors can be supplied with electrical power via a DC offset superimposed on the transmitted electrical signals. The sensor modules can electrically connect to cables of the network via a clamp that includes an insulation-piercing probe placed in direct contact with an electrical conductor of the cable.

The above summary does not include an exhaustive list of all aspects of the present invention. Indeed, the inventors contemplate that the invention includes all systems and methods that can be practiced from all suitable combinations of the various aspects summarized above, as well as those disclosed in the detailed description below and particularly pointed out in the claims filed with the application. Such combinations have particular advantages not specifically recited in the above summary.

DESCRIPTION OF PREFERRED EXEMPLARY EMBODIMENTS

A distributed sensor array system according to various aspects of the invention provides numerous benefits including comprehensive detection of reservoir contamination. As discussed in detail below with reference to exemplary embodiments employing a single sensor array 110 (FIG. 1) and a pair of sensor arrays 510, 540 (FIG. 5), such a system transmits data representative of a level of impurities in the reservoir fluid from a number of sensors immersed in the reservoir.

Figure 1:
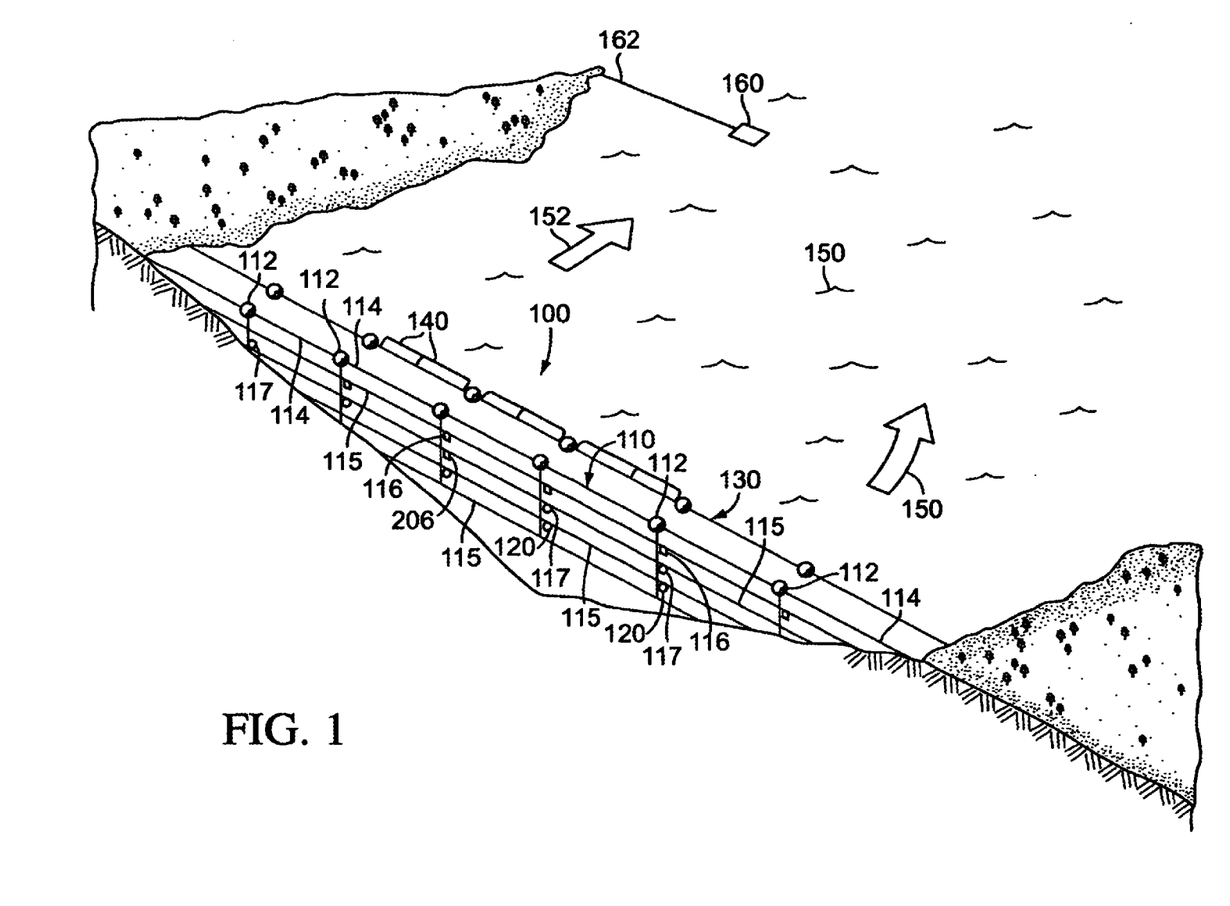
FIG. 1 is a cutaway perspective view of a reservoir containing a single-network distributed sensor array system according to various aspects of the invention.

Distributed sensor (i.e., detector) array system 100 of FIG. 1 is immersed in a reservoir 150 with sensor modules 112, 116, 117, 120, 206 distributed throughout a cross section of reservoir 150 from its surface to near its bottom. System 100 includes a cable network 110 of (1) horizontal cables, which include a top supporting cable 114 and subordinate cables, e.g., cable 204, and (2) crossing vertical cables, e.g., cable 202. Top supporting cable 114 connects between surface modules 112, which perform a dual role as both surface-level sensor devices and flotation devices. Exemplary modules 112 include foam structure of sufficient buoyancy to assist supporting cable 114 in its task of supporting remaining structure of network 110.

A cable network according to various aspects of the invention includes any structure suitable for fixedly supporting (i.e., keeping in substantially fixed positions) a plurality of sensor modules in a desired arrangement within a body of fluid. Exemplary cable network 110 of system 100 includes a number of vertical and horizontal cables that intersect to form rectangular subsections, preferably large enough to permit marine life of all expected sizes to pass through without obstruction. In variations with diagonal cables, such subsections can be diamond shaped or triangular and of sufficient dimensions to avoid disrupting marine life.

Cable network 100 is shown with its cables in a vertical plane. In variations, the plane is curved to surround a shore point (e.g., a water intake point) or tilted such that the top is closer to or farther from shore than the bottom. Cables are substantially in a common plane, as the term is used herein, whether they are arranged as in such curved and tilted variations or lie in a strict plane as illustrated in FIG. 1, so long as they do not cross each other as viewed from above.

Immersed detector (i.e., sensor) modules 116, 117, 120 suspend from crossing cables of network 110 in rows at a "least depth" level, an "intermediate depth" level, and a "maximum depth" level, respectively. (Also at the "intermediate depth" level is an exemplary sensor module 206 that is discussed in greater detail below.) Variations of system 100 can employ different types of sensors at different depths in reservoir 150. For example, sensors of "maximum depth" modules 120 can be responsive to the presence of heavier-than-water or particulate contaminants that can be expected to gradually sink downward. Sensors of "surface-level" modules 112 can be selected for responsiveness to lighter-than-water contaminants, e.g., hydrocarbons, which can be expected to remain at or near the surface of reservoir 150.

Reservoir 150 of FIG. 1 has a pumping station 160 and municipal water main 162, and distributed sensor array system 100 is advantageously placed upstream of those elements. A monitoring station (not shown) in pumping station 160 analyzes data from sensor modules of network 110 that is representative of the level of impurities in the water, suitably alerting responsible personnel upon detection of an unacceptable level of impurity.

The level of an impurity in a fluid is a metric suitable for determining whether a problem exists as to the purity of the fluid, e.g., a chemical, biological, or radioactive signature that could indicate tampering or terrorist attack. The metric can be a quantized one. For example, there can be a simple binary result indicating that the impurity concentration, mass, particle count, etc. is above a predetermined threshold. Another type of quantized metric can indicate which of a number of impurity ranges the impurity concentration, mass, particle count, etc. falls within. Alternatively, the metric can be a substantially continuous indication of impurity concentration, mass, particle count, etc.

As FIG. 1 illustrates with arrows 152, water of reservoir 150 reaches sensor modules 112, 116, 117, 120 suspended on network 110 of system 100 before it reaches pumping station 160. Prompt manual action or an automated response to shut off pumping station 160 can prevent downstream contamination before the water column in the vicinity of system 100 reaches pumping station 160 or before contaminants migrate to water in the vicinity of pumping station 160.

A distributed sensor array system according to a particularly advantageous aspect of the invention includes one or more decontamination subsystems to permit faster response to a contamination situation even while the presence of such a situation is being detected. For example, system 100 includes a float-supported cable span 130 with oil-absorbing devices 140 attached along its length. In variations, the decontamination subsystems (e.g., copolymer-based oil-absorbing devices) have sufficient buoyancy to support themselves without additional floats.

Oil-absorbing devices, which can be of the type disclosed in U.S. Pat. Nos. 6,143,172 and 6,344,519 to Rink et al. (referred to herein as the '172 and '519 patents, respectively, and incorporated herein by reference), can be included in array 110, for example by loose connection to or inherent construction with top cable 114. One such device, sack 10 of the '172 patent's FIG. 2, can attach to the cable of span 130 using the eye 80 of sack 10 of that patent via a suitable attachment structure not shown, e.g., a turnbuckle or rope pigtail.

A distributed sensor array system according to various aspects of the invention employs information-transmissive cables to convey information from all or a subset consisting of a plurality of its various distributed sensors to a collection point, which typically conveys the information to a remotely located monitoring destination, likely outside a reservoir. The particularly advantageous configuration of system 100 for electrically and mechanically connecting fluid contamination sensors and cable network may be better understood with reference to FIG. 2.

Figure 2:
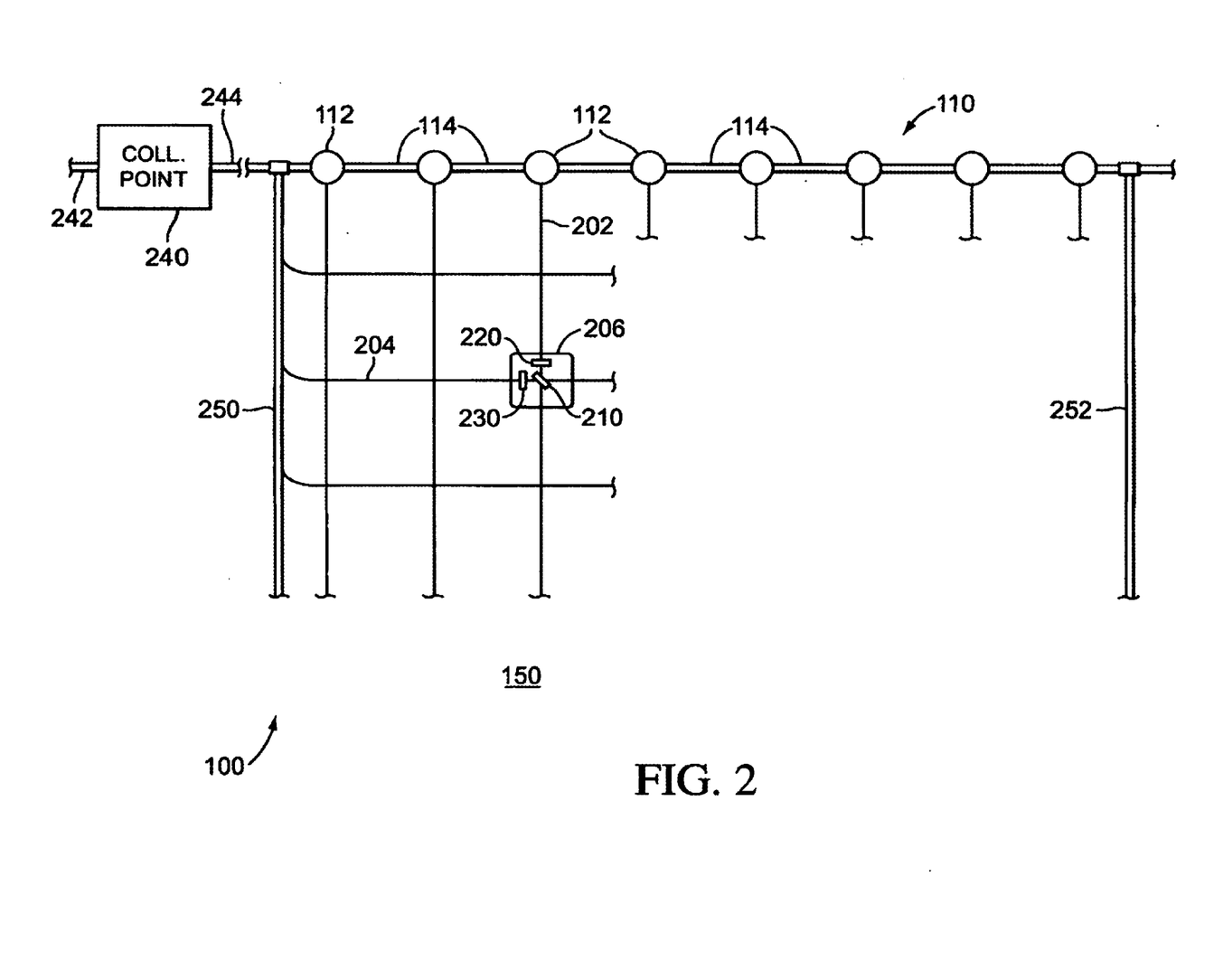
FIG. 2 is a partial side view of the system of FIG. 1, illustrating connection of one sensor module to a pair of intersecting cables.

As FIG. 2 illustrates, exemplary system 100 includes a collection point 240 electrically coupled via a master trunk cable 244 to a network 110 that suspends almost completely immersed in a reservoir (not shown) by floats 112. Network 110 is made up of a number of horizontal signal cables, one of which is a horizontal trunk cable 114 and an exemplary horizontal cable 204 that connects to one sensor module 206 illustrated in FIG. 2. Network 110 further includes a number of vertical ground cables, one of which 202 connects to module 206, and trunk vertical cables 250, 252. One side of collection point 240 electrically couples to the sensor modules of network 110 via trunk cable 244 which contains electrical connections to horizontal and vertical trunk cables 114, 252, 254 and subsequently to the various cables at which the sensor modules attach. An opposite side of collection point 240 couples to the monitoring station discussed above (e.g., inside pumping station 160 of FIG. 1) through a wide-area network connection cable 242 as well as other structure (e.g., a DSL modem, TCP/IP packet routers) not shown.

A collection point according to various aspects of the invention includes any structure suitable for providing a common point of connection to sensors (typically through sensor modules, as discussed below) of a cable network or interconnected networks. When isolation between the various circuits leading to different sensors is not an issue, a collection point can be as simple as an a common electrical connection of the circuits. Preferably, however, a collection point includes circuitry to isolate the various circuits from each other while permitting them all to suitably influence the common output of the collection point and respond to its common input. For example, exemplary collection point 240 includes summing circuitry (not shown) that adds up the signals from each sensor module of network 110 to generate a common output signal at cable 242, and splitting circuitry (not shown) that conveys a common input signal at cable 242 to the sensor modules. Collection point 240 can be integrated with the monitoring station (not shown) or located at a point along master trunk cable 244 between the station and network 110, either inside or outside reservoir 150.

Because ground cables need not be insulated, they are particularly suitable for structural support of sensor modules. Thus it is advantageous for the vertical cables of network 110, which support the non-buoyant weight of sensor modules in system 100, to be ground cables, while the horizontal cables are thinner and insulated. The horizontal cables perform a relatively minor structural role of keeping the vertical cables of network 110 substantially in a common plane.

In a variation where the simplicity and other benefits of having sets of cables substantially in a common plane is not required, a different geometrical arrangement can be employed. With suitable supporting or tensioning structure, for example, sets of cables can be arranged substantially in a common two-dimensional manifold (e.g., a conic or cylindrical section) that is not necessarily a plane.

System 100 transmits information via electrical signals conducted by electrical circuits that include pairs of intersecting cables, connected in series, of network 110. For example, electrical signals transmit from sensor module 206 to a collection point 240 via a circuit that includes, in series, top supporting cable 114, vertical cable 202, horizontal cable 204, and trunk vertical cable 250. The electrical circuit between network 110 and module 206 completes through clamps 220, 230.

The single signal cable conductor conveys power, clocking signals, and bidirectional communications between sensor modules and the host. Advantageously, system 100 performs bidirectional communications via signal cables having only a single electrical conductor. (A conductor can be, e.g., a single copper strand or group of strands in an otherwise steel cable.) The electrical circuits complete through ground cables (e.g., 202) that need not be insulated, removing the need for a return or ground conductor in the signal cable itself.

Redundancy and the increased reliability that it provides can be achieved with additional electrical circuits that include a portion (not shown) of horizontal cable 204 connecting from sensor module 206 to vertical trunk cable 252, or a portion (not shown) of vertical cable 202 connected to a bottom anchor cable (not shown), or both.

According to a particularly advantageous aspect of the invention, a distributed sensor array system employs unitary cables having both information transmission and support functions. The system can employ any type of cable suitable for both structural support and transmission of information. For example, circuits of bare or insulated single-conductor wire cables can transmit via electrical signals at modest frequencies. Single lengths of coaxial cable can transmit information via high-frequency electrical signals. Cables including structural strands (e.g., twisted steel wires) and one or more "piggybacking" strands of optical fiber can transmit information via contained electromagnetic radiation in the vicinity of optical wavelengths. Information-transmissive strands of a cable can piggyback with structural strands of the cable inside a hollow core of a surrounding structural strand bundle, or by wrapping around the exterior of a structural strand bundle, or by any other suitable technique.

In a variation, network 110 is configured for information transmission only in horizontal cables (e.g., cable 204), each one of which transmits information (e.g., as electrical signals) for sensor modules (e.g., module 206) suspended by that particular cable. A single coaxial cable can transmit information electrically via a circuit formed by the cable's center conductor and surrounding shield conductor. In such a variation, vertical trunk cables 250, 252 provide trunk connections (separately or redundantly) between all of the horizontal cables and collection point 240. Vertical cables (e.g., cable 202) of network 110 then serve only a structural purpose. A trunk connection can have separate coaxial cables for each individual connection or can have individual connections multiplexed (e.g., by a suitable form of one of the multiple access schemes discussed below) onto a single trunk cable.

In another variation of network 110, top supporting cable 114 provides a trunk connection as in the variation discussed above, but with trunk vertical cable 250, cable 252, or both providing redundant trunk connections along horizontal cables that are also information-transmissive. The redundancy provided by such a variation may be desirable, despite its added cost, in particularly failure-intolerant implementations.

A sensor according to various aspects of the invention includes any structure that is suitable for attaching (preferably in a releasable or modularly attachable fashion) to a cable network immersed in a reservoir of liquid to detect a contaminant in that liquid and transmit data representative of the liquid's purity. Typically but not necessarily, a sensor is housed in a sensor module, which supports it, channels fluid through or around it, and converts its raw output into suitably modulated and networked signals.

Figure 3:
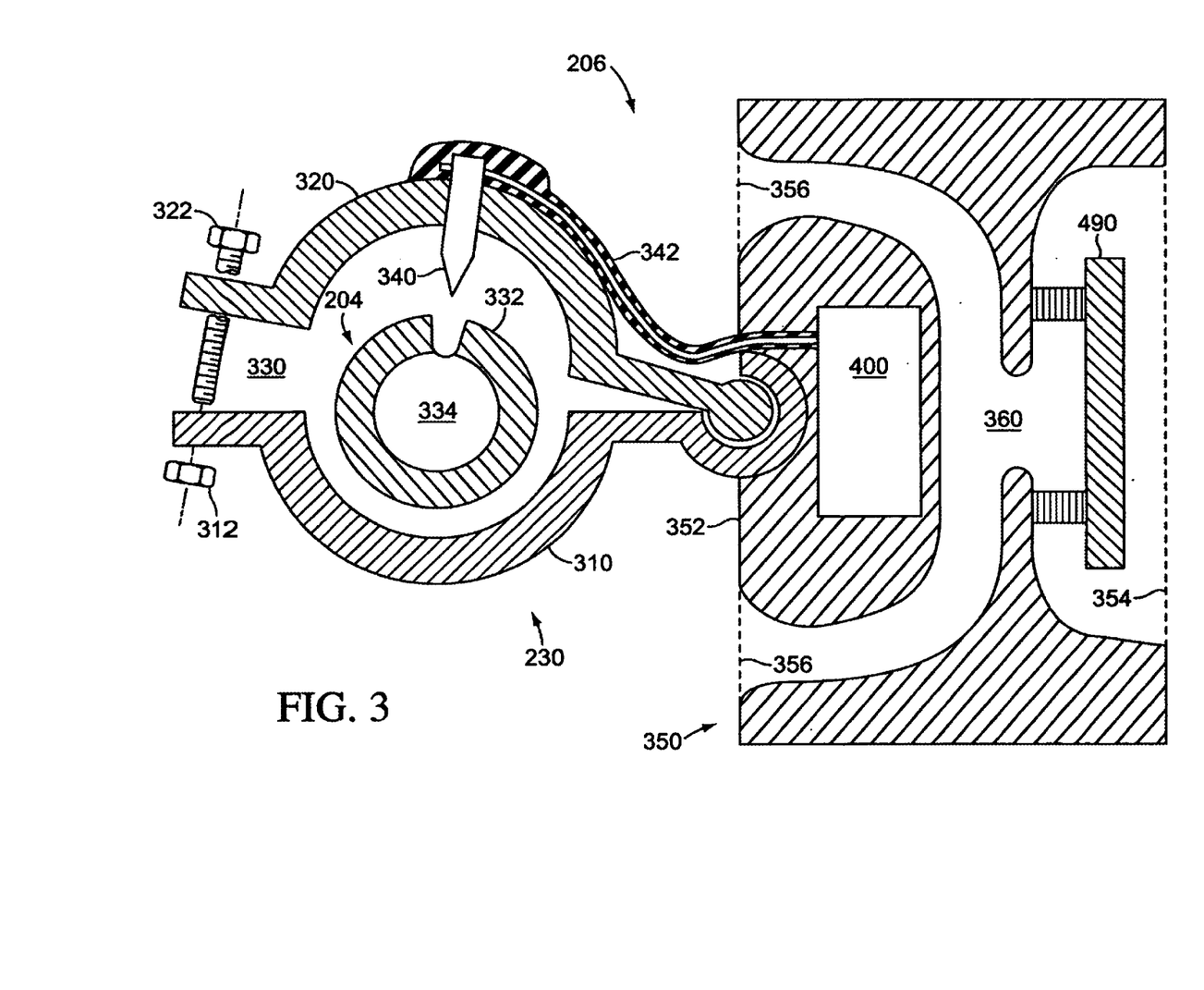
FIG. 3 is a cutaway side view of a sensor module according to various aspects of the invention, illustrating an exemplary electrical connector and sensor arrangement.

As may be better understood with reference to FIG. 2, for example, sensor module 206 releasably attaches to cable network 110 via a releasable clip 210, which holds module 206 at the interconnection of cables 202, 204. Clip 210 thus frees the electrical connections of clamps 220, 230 from providing the bulk of such support. An additional function performed by clip 110 is to secure cables 202 and 204 together at the point where they intersect, limiting abrasive damage to the cables by preventing relative movement at that point.

Clip 210 can be a simple disposable plastic cable tie that passes around the intersection of cables 202, 204 and through suitable recesses (not shown) in rear face 352 of a housing 350 (FIG. 3) of module 206. The cable tie of clip 210 can simply be cut when sensor module 206 is to be released from cable network 110. In variations where permanent, releasable structure is preferable, sensor modules according to various aspects of the invention can employ suitable fasteners such as threaded bolts or nuts and mating mounting hardware to releasably attach to a cable network. Sensor modules can be added (and, if releasable, removed) as needed, such as in response to particular threats or the emergence of perceived contaminants of concern.

As may be better understood with reference to FIG. 3, for example, sensor module 206 includes a housing 350, which has an interior recess 360 and a clamp 230 (discussed briefly below with reference to FIG. 2) that attaches to one side 352 of housing 350. Clamp 230 includes lower and upper half shells 310, 320. Interior recess 360 of housing 350 is accessible by fluids outside housing 350 via perforated screens 354, 356. An electronics subsystem 400 resides in module 350.

Clamp 230 and its counterpart clamp 220 (FIG. 2) facilitate electrical and mechanical connection between module 206 and network 110. Having such a clamp connect directly to the supporting and information-transmissive cable avoids the expense of mechanical and electrical connectors for each of the many possible sensor modules that can be included. As illustrated in FIG. 3, first half shell 310 of clamp 230 hingedly connects to second half shell 320 and also to housing 350. That arrangement allows half shell 320 to move away from half shell 310 so that clamp 230 can pass over a cable 204 through a gap 330, allowing cable 204 to rest in a recess between half shells 310, 320.

When half shells 310, 320 close together with a bolt 322 and nut 312 combination, clamp 230 makes both an electrical and a mechanical connection between sensor module 206 and horizontal cable 204. In the example of FIG. 3, cable 204 is insulated and fits snugly between closed half shells 310, 320. A conductive needle 340 pierces insulation 332 of cable 204, making electrical connection between conductive portion 334 of cable 204 and half shell 320. An insulated wire 342 electrically connects needle 340 to electronics subsystem 400.

Suitable structure (not shown) for facilitating a watertight seal can be included on the sides of half shelves 310, 320. Such a seal can be desirable to prevent corrosion of needle 340 and conductive portion 334 of cable 204, and to avoid migration of water between insulation 332 and conductive portion 334 of cable 202. Conductive needle 340 is preferably fabricated from a corrosion-resistant alloy (e.g. stainless steel), and preferably of the same substance as cable 334 to minimize galvanic corrosion. In the example, the half shell is made of electrically insulating material, such as hard plastic.

In some situations, moderate water leakage through insulation 332 can be accommodated without loss of function of the clamp. A slight but tolerable loss of power efficiency might be incurred by electrical conduction from the horizontal clamp to the vertical clamp, moderated by the limited conductivity of the water (especially freshwater) across the distance between clamps.

In a variation, a half shell is made of conductive material, preferably including a coating of noncorrosive material. The half shell of such a variation itself provides an electrical connection between the cable enclosed within it and the sensor module to which it makes mechanical connection.

In the exemplary configuration of FIG. 2, vertical ground cable 202 is of the same type as cable 204, and clamp 220 includes half shells of the same type as clamp 230. However, ground cable 202 can be non-insulated and connect with a simple electrical clamp instead of the "vampire" clamp 230 discussed above with reference to FIG. 3.

With a non-insulated ground clamp, cable, or both, the surrounding reservoir or water body itself provides a certain degree of grounding aside from the ground-connected cable. Signal wires need to be more protected, especially in salt water environments where the electrical conductivity is much higher than in fresh water. A bare metallic conductor, whether in a standard electrical clamp or in a non-insulated electrical cable, should be protected against corrosion.

Metallic conductors can be protected from corrosion using anodization, galvanization, or by the addition of a sacrificial cathode, such as a zinc "getter," in the vicinity of the exposed metal surface. Sacrificial zinc cathodes are effective on a distance scale of meters. Therefore the placement of a sacrificial zinc cathode on a sensor could provide effective corrosion protection for the bare metal cables of conductor 202. Avoiding direct contact of dissimilar metals is another effective measure to minimize corrosion.

As may be better understood with reference to FIG. 3, exemplary sensor module 206 includes a sensor 490 that is mounted in a recess of housing 350 behind a perforated screen 354. When module 206 has face 352 with its perforated screens 356 oriented toward current flow in reservoir 150 and perforated screen 354 facing away from the current flow, or vice versa, water of reservoir 150 can pass through interior channel 360 of housing 350 and pass around (or through) sensor 490 on its way in or out.

Figure 4:
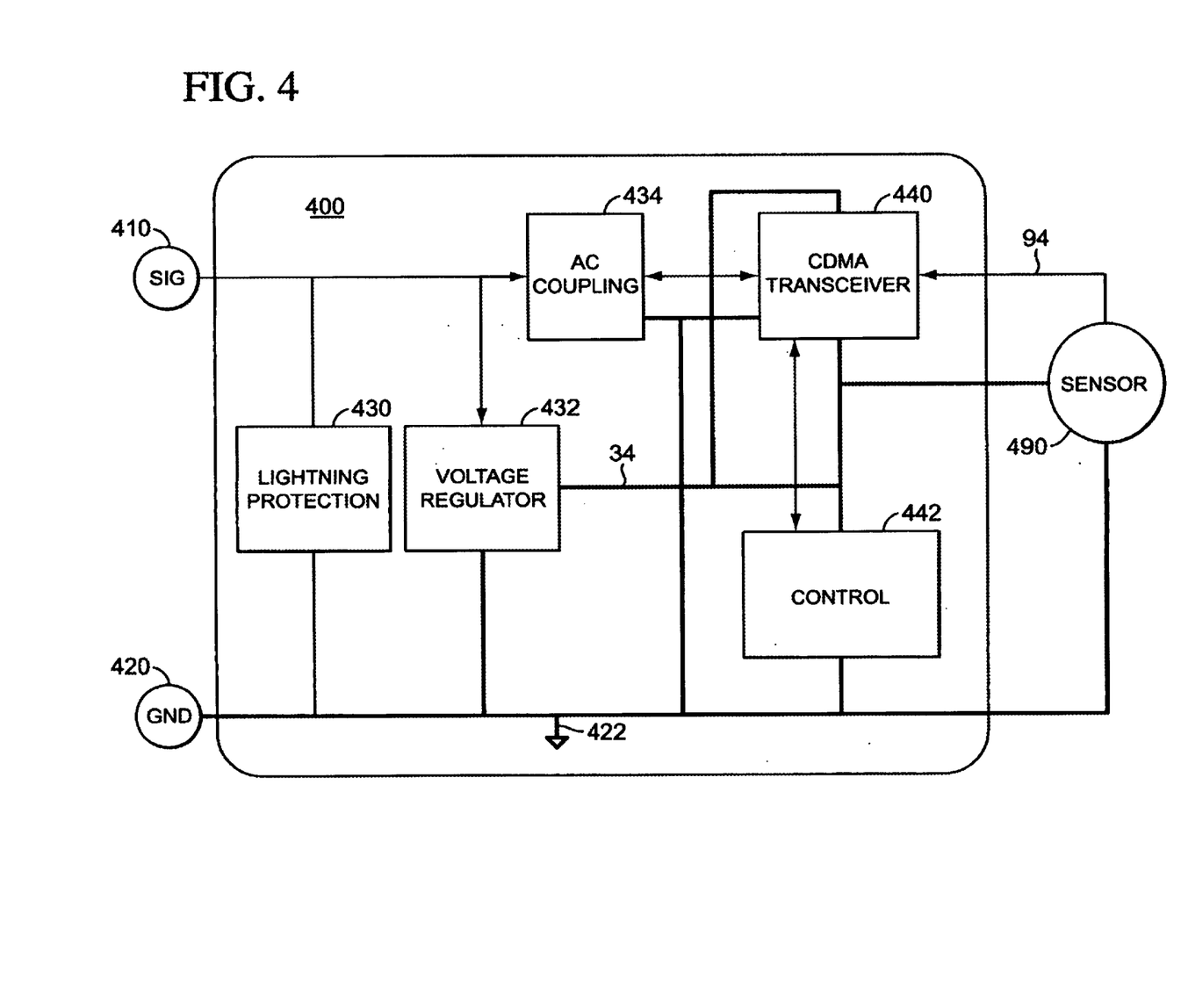
FIG. 4 is a schematic block diagram of electrical circuitry in the sensor module of FIG. 3.

Sensor 490 transmits data, in the form of an analog signal that is proportional (e.g., linearly or logarithmically) to a level of fluid impurity, to electronics subsystem 400 of sensor module 206, which transmits modulated digital data based on the analog data to collection point 240 (FIG. 2). Sensor 490 can be of any type suitable for generating a signal to indicate the degree to which particular type or types of contaminants are present in the liquid surrounding it. (Examples of different types of sensing that sensor 490 can perform are discussed below.) The signal transmits to electronics subsystem 400 via a suitable cable, which FIG. 4 represents schematically as signal line 94. Preferably, all sensor modules in a given distributed sensor array system have a standardized shape and maintain information transmission with a common protocol and signal type. In variations where the simplicity of a level-proportional analog signal is not required, a sensor can provide a more complex type of output such as digitally encoded data or a modulated analog signal.

As may be better understood with reference to FIG. 4, electronics subsystem 400 includes a suitable signal connector 410 and ground connector 420, which connect electronics subsystem 400 to wire 342 and the conductive chassis of housing 350 (FIG. 3), respectively. Inside subsystem 400, connectors 410, 420 connect directly to lightning protection circuitry 430, a voltage regulator 432, and AC coupling circuitry 434. Subsystem 400 further includes a code-division multiple access (CDMA) transceiver 440 and a control subsystem 442.

Under control of subsystem 442, CDMA transceiver 440 obtains information about the presence or absence of contaminants from sensor 490 and transmits that information, in the form of a direct-sequence spread spectrum (DSSS) signal through AC coupling circuitry 434, onto signal cable 410 and ultimately to collection point 240 (FIG. 2). Frequency-hopping spread spectrum can be suitably employed instead of DSSS.

Exemplary electronics module 400 includes lightning protection circuitry 430 because protection against electromagnetic impulses (EMP) is important for maximum reliability. Any long lengths of cable on the ground, in the air or in the water are subject to lightning and other EMP events. Such events may be natural or may be caused by terrorist organizations employing EMP weapons. Coaxial shielding can provide some benefits for EMP shielding by protecting the signal wire from direct exposure to electromagnetic pulses. For high pulse voltages however, eddy image currents will still be induced in the central conductor.

The most vulnerable parts of system 100 (FIG. 2) to EMP, for example, are top supporting cable 114, floats 112, and connectors and land lines (not shown). Those elements can propagate EMP events into the underwater sensor modules. Therefore, EMP protection is needed for the underwater sensor modules as well as collection point 240 and (in embodiments employing them) for surface surface sensor modules. For example, electronics subsystem 400 (FIG. 4) of sensor module 206 employs lightning protection circuitry 430 to create a shunt to ground in the presence of rapid-onset electrical impulses having damagingly high-voltage, e.g., from a lightning strike to network 110. Circuitry 430 can employ any suitable type of component or components for this purpose, e.g., one or more avalanche breakdown diodes or metallic-oxide varistors (MOVs). A series resistance can be placed between connector 410 and circuitry of subsystem 400 for additional protection during any turn-on interval of lightning protection circuit 430.

Voltage regulator 432 supplies power on a line 34 that is kept substantially within a predetermined range, for manageable input voltages in the range of 6.5–65 volts DC. Sensor module 206 receives electrical power from collection point 240 (FIG. 2) via signal cable 204 in the form of a DC offset that is superimposed on whatever type of electrical signaling collection point 240 and its sensor modules employ for information transmission. Using any suitable circuitry, e.g., a MAXIM 5023 DC integrated circuit, voltage regulator 432 converts the 6.5–65 volt DC offset to a lower voltage such as +3.3 or +5 volts that is suitable for microelectronic circuitry in code-division multiple access (CDMA) transceiver 440, control subsystem 442, and sensor 490.

When an efficient voltage regulator is employed, the use of a relatively high DC offset, e.g., at a 10:1 ratio over the actual voltage needed, can make transmission of power more efficient over long lengths of cable. Less current is required to convey a given amount of power at the higher voltage, and resistive power loss in the cable is proportional to the square of the current.

In a variation, collection point 240 supplies AC power on the signal cables for the individual sensor modules to convert into DC voltage for their internal circuitry. AC power can propagate through suitable capacitive or inductive circuitry without a galvanic connection, which could be useful in some situations. However, using only DC power may be preferable in a saltwater environment to minimize field losses in the power cable and surrounding conductive seawater. The selection of DC or AC power transmission can be made based on cost vs. performance analysis at the module level. Selecting a system for maximum reliability may be desirable to minimize maintenance costs.

In electronics subsystem 400 of exemplary sensor module 206, CDMA transceiver 440 transmits and receives information, without any DC offset from the superimposed power supply current, through AC coupling circuitry 434. The information, which can be left in baseband form or modulated, undergoes transformation into a DSSS signal to advantageously permit collision- and multipath-resistant multiple access on a transmission medium shared with other sensor modules, i.e., signal cable 204. Transceiver 440 transforms the information into a spread spectrum signal by convolving it, e.g., subjecting it to binary phase-shift keying (BPSK) modulation, with a unique code. The code consists of a repeating sequence of varied baseband amplitude levels or carrier frequency characteristics (typically, phase). For example, CDMA transceiver 440 convolves baseband digital information into BPSK-modulated transmissions to collection point 240 with a unique "Gold" code or "Walsh" code that is orthogonal (in a signal processing sense) to codes used by other sensor modules (not shown) that simultaneously transmit to collection point 240 over the same signal cable 204.

Collection point 240 (FIG. 2) combines CDMA-modulated signals received from sensor modules 112, 116, 117, 120, and 206 (FIG. 1), preferably with a simple summing operation. Collection point 240 transmits the combined signals, multiplexed by orthogonal convolution codes rather than separate electrical conductors, to the monitoring station (not shown) via connection 242.

A counterpart CDMA transceiver (not shown) in the monitoring station convolves the aggregate incoming signal it receives via cable 204 with separate codes corresponding to each sensor module with which it is in communication via cable 204. That second convolution de-spreads the signal into a rendition of the original baseband or modulated data. Other signals having different spreading codes are reduced by convolution to (ideally) zero amplitude, when orthogonal codes are used. Any interfering narrowband signals that signal cable 204 picks up are convoluted into what appears to be wideband noise, with significantly reduced spectral content remaining in the baseband frequency range of interest. When 100-chip/bit Gold codes are employed, this reduction (also known as process gain) is on the order of 20 dB.

In variations where the benefits of multiple access to a shared transmission medium are not required, sensor modules can transmit and receive baseband data (e.g., direct changes in line voltage proportional to data) or modulated data via separate cables to a collection point that conveys each cable's signal to a monitoring station via a dedicated strand of a cable having multiple separately information-transmissive strands.

As illustrated in FIG. 1, the sensor modules of system 100 are arrayed in substantially a regular two-dimensional array. Cable network 110 is of substantially rectangular shape, with vertical and horizontal cables, but variations employing diagonal cables (e.g., oriented at angles of about 45° and 135° relative to vertical) can also be employed. The regular two-dimensional array arrangement has a significant benefit in that cable is efficiently used and the sensor modules are in an orderly layout of rows and columns. As may better understood with reference to FIG. 5, however, all reservoirs cannot be expected to have a subsurface profile that is amenable to full coverage with a rectangular array of sensor modules.

With suitable deployment of separate but interconnected sensor arrays, a distributed sensor array system according to various aspects of the invention can position sensor modules precisely in two or even three dimensions in a reservoir's water column. The position of the sensor modules can optimize surface sensing, bottom sensing, or overall sensing within the water column. With a suitable combination of arrays at different depths in a reservoir, a system with multiple distributed sensor arrays can provide coverage even of reservoirs having irregular bottom topography. For example, distributed sensor array system 500 of FIG. 5 effectively monitors contaminants across the irregular subsurface profile 516 of a reservoir 502 by employing two sensor arrays 510, 540 at the bottom and top, respectively of reservoir 502.

Figure 5:
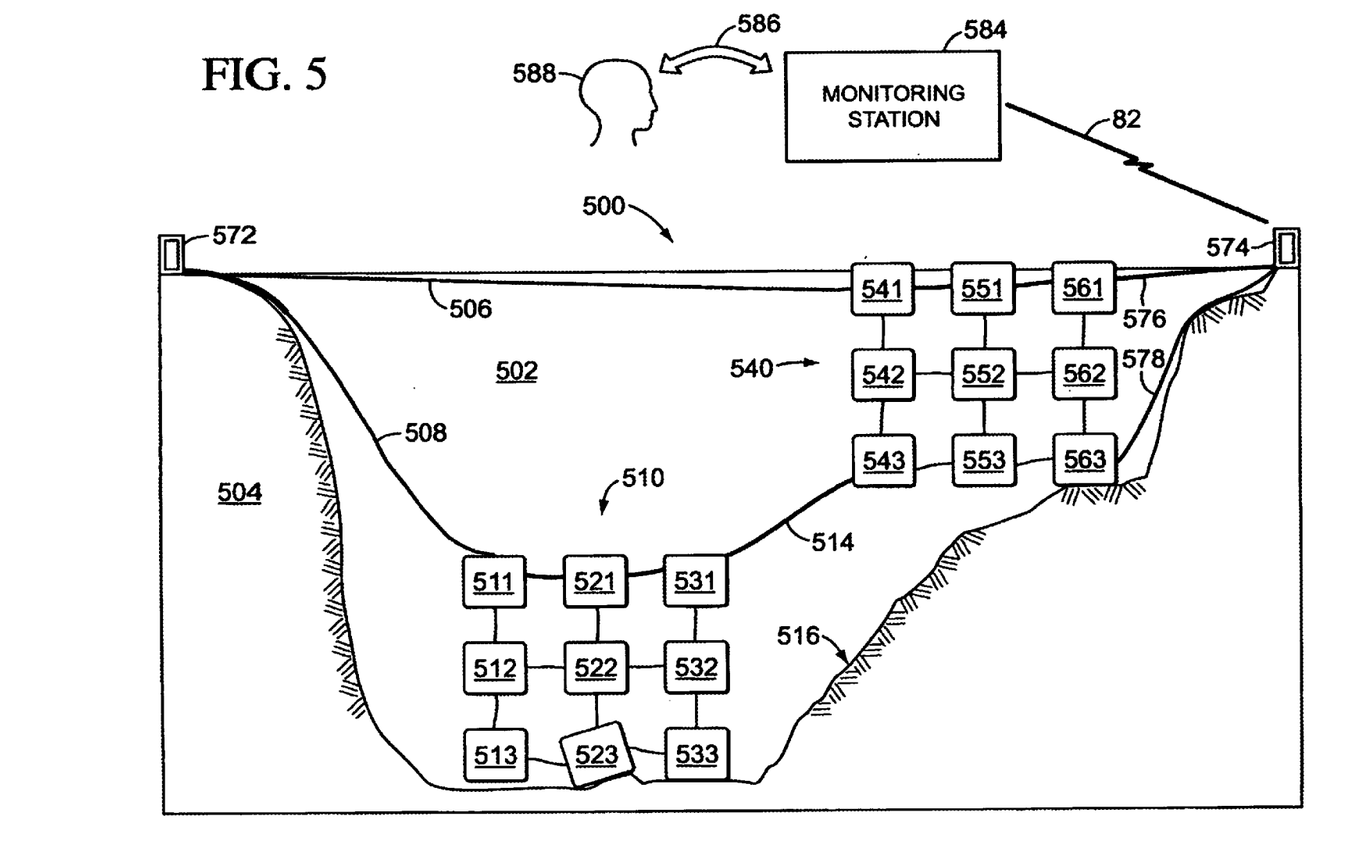
FIG. 5 is a cutaway side view of a multiple-network distributed sensor array system according to various aspects of the invention, in a reservoir having an irregular bottom profile.

In addition to arrays 510, 540, system 500 includes a monitoring station 584 outside reservoir 502, e.g., in a pumping station (not shown), shore connection structures 572, 574, and various trunk or supporting cables 506, 508, 514, 576, 578. Monitoring station 584 is under observation or control of an operator 588, locally or remotely, through conventional human-computer interaction represented by arrow 586. Top cables 506, 576 connect to opposite sides of sensor arrays 540, maintaining tension in the mechanical connection between a top row of buoyant sensors 541, 551, 561. Shore connecting structures 572, 574 suitably provide mechanical anchoring of top cables 506, 576, respectively. Cables 508, 514 connect to opposite sides of fully immersed sensor grid 510, directly supporting a top row of sensor modules 511, 521, 531 of grid 510 and indirectly supporting a middle row of sensor modules 512, 522, 532 and a bottom row of sensor modules 513, 523, 533.

Monitoring station 584 maintains bidirectional communication via a wide-area network connection 582 with shore connection structure 574, which suitably relays communications between monitoring station 584 and sensor modules of grids 510, 540. In addition to supporting grid 540, cable 576 also serves as a trunk cable for relayed information transmission between sensor modules 541–563 of grid 540 and monitoring station 584. Similarly, cable 514 serves as a trunk cable for relayed information transmission between monitoring station 584 and sensor modules 511–533 of grid 510. In a variation employing single-wire and non-insulated ground connections without multiplexing, each sensor module 511–533 of grid 510 transmits information to shore connection structure 574 via an electrical circuit that includes one strand (not shown) apiece of cables 508, 506, 576, 578, and 514, in series.

Distributed sensor arrays can secure in position and orientation within a reservoir by weights, floats, or suitable combinations of weights and floats. By adjusting the size of the floats and thus their buoyancy, the arrays can be in a "surface detector" position or in a "bottom detector" position in which sensor modules are completely immersed and touch the reservoir bottom. For example, a distributed sensor array in a "bottom detector" position can be deployed next to, e.g., between, two "surface detector" arrays.

A monitoring station according to various aspects of the invention includes any hardware or combination of hardware and software, typically located within a pumping station facility, that is suitable for maintaining communication with a plurality of sensor modules immersed in a reservoir to receive data representative of reservoir purity from the modules. For example, monitoring station 584 of system 500 (FIG. 5) includes a suitable computer (not shown) running an operating system (e.g., Linux®, Microsoft Windows®), sensor module supervision software, and remote access server software (e.g., an httpd with cgi scripts, ssh, vncserver).

Monitoring station 584 provides central processing of the data and uplink and notification to governmental agencies in the event of a detected threat. It provides power, synchronization, and bidirectional data communications to sensor modules 511–533, 541–563 of system 500, analyzing and recording data from them and making the information available over secure (e.g., SSL, VPN) connections to remote sites. An operator can collect the data and preserve it in the event of data loss by the municipality. The data can assist the operator in planning for improved detector module and system reliability.

Figure 6:
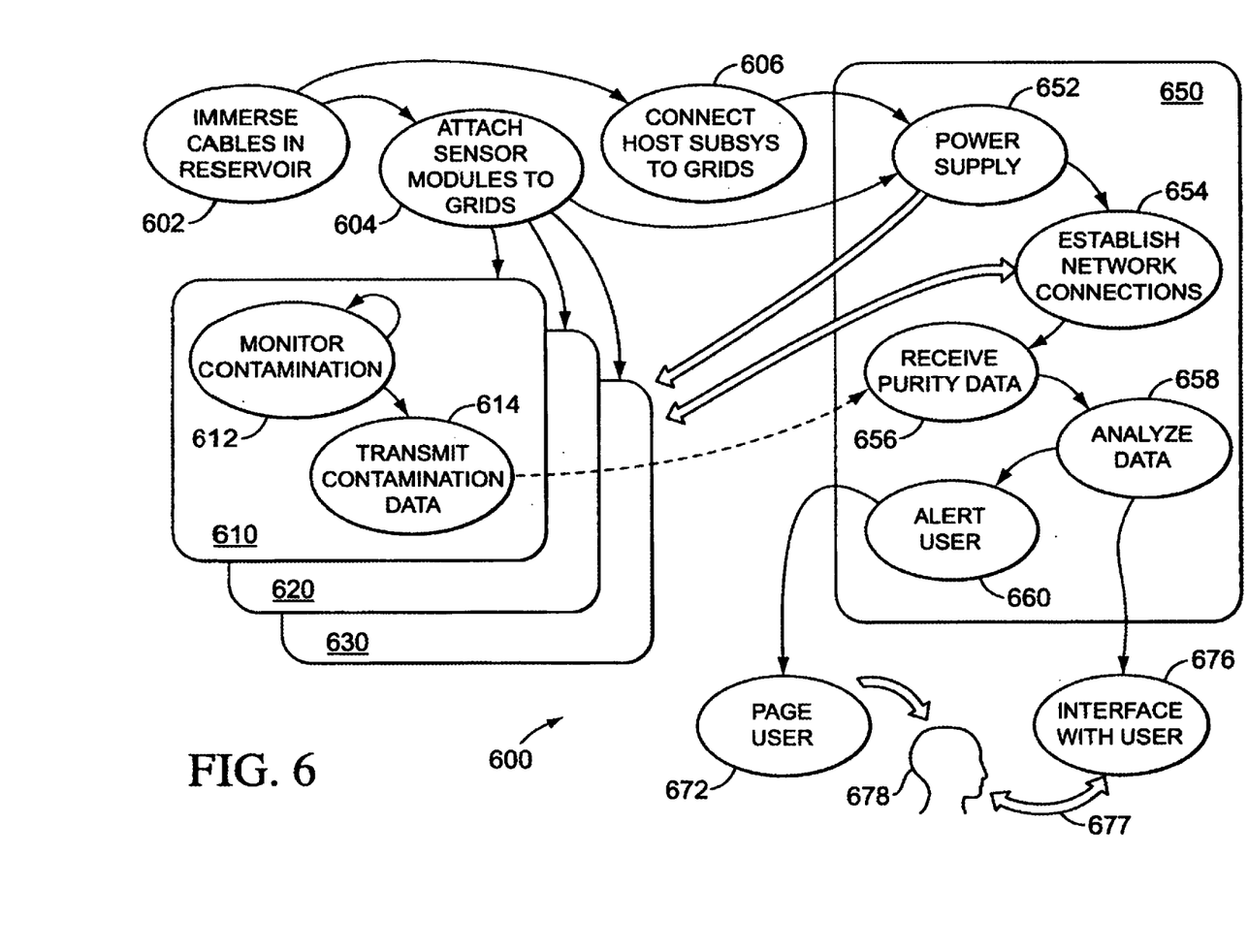
FIG. 6 is a data flow diagram of a method of the invention for monitoring purity of a reservoir.

A method of the invention for monitoring purity of a reservoir, for example employing various components of system 500 (FIG. 5), may be better understood with reference to the data flow diagram of FIG. 6. Exemplary method 600 begins with deployment processes 602–606. At process 602, workers immerse cables of system 500 in reservoir 502 with no sensor modules yet attached. Floats and weights or anchors (not shown) can attach at various points on the cables, e.g., floats at supporting cables 506, 576, in place of buoyant and anchoring sensor modules.

Upon completion of process 602, workers connect monitoring station 584 to arrays 510, 540 through shore connecting structure 574, at process 606. If monitoring station 584 resides in a pumping station somewhat downstream from arrays 510, 540, for example, the connection can include a suitable wide-area network link between shore connecting structure 574 and subsystem 584.

At process 604, which can occur shortly after cables are immersed in reservoir 502 at process 602 or at any other desired time, workers attach sensor modules 511–333 to a cable grid of array 510 and sensor modules 541–363 to a cable grid of array 540. Rather than attaching all of these sensor modules, process 604 can involve attachment of only a subset of them. Any desired type of subset can be employed for a particular deployment requirement. When detection of contaminants at a pumping station's surface level is critical, for example, initial deployment at process 604 can consist only of sensor modules 541–363 of array 540. Sensor modules of 511–333 can be deployed later if a deep-water contamination threat becomes of concern. As another example, a subset consisting of sensor modules sensitive to common contaminants can be initially deployed at process 604 with wide deployment of more specialized sensor modules when a particular threat is discerned.

With processes 604, 606 complete, monitoring station 584 continues operations of method 600 with a group 650 of processes 652–660. Process 652 supplies power (e.g., via a DC offset) to the sensor modules. Process 640 establishes network connections with the powered-up sensor modules, which perform their individual monitoring and information transmission processes, exemplified in FIG. 6 by process group 610–630.

FIG. 6 illustrates processes of an exemplary sensor module's process group 610. After the power-up by process 652 and the establishment of network connections by process 654, a sensor module process 612 monitors contamination of reservoir 502. Process 612 conveys information about contaminant levels to process 614, which transmits data representative of that information to process 656 of monitoring station process group 650.

Process 656 relays the received data to process 658, which analyzes the data to generate meaningful results for a human operator 678. Results of analysis process 658 can include estimates of contaminant levels (e.g., in mg/liter) along with ranges of acceptable levels, simple on/off hazard alerts, trend reports showing contaminant levels over time, and statistical reports showing average contaminant levels with standard deviation statistics or confidence intervals. Process 658 can employ any suitable software for its implementation.

With an electronic page, cellular telephone instant message, e-mail, or other type of electronic paging technique or combination of such techniques, process 660 alerts operator 678 (along with any other responsible personnel) when it receives an indication from process 658 that a hazard condition exists. In addition to simply alerting operator 678 of the hazard condition without providing details, process 660 can include brief information about the type and urgency of the hazard, as appropriate for the type of paging technique being employed. For example, a first-time detection of a particular type of biological contamination hazard might signal a homeland security authority to issue a nationwide terrorism alert in addition to paging authorities who are responsible for the local reservoir where the hazard was detected.

A user interaction process according to various aspects of the invention can be implemented with any combination of hardware and software suitable for permitting a user to select and view analysis results. For example, process 676 is implemented by a suitable client and server combination that renders a conventional hypertext display and solicits form input (e.g., radio buttons, check boxes, text fields). The server (not shown) includes a conventional computer hardware and software combination implementing an HTTP server, a forms processor, and a suitably firewall-protected interface to a wide-area network. The client (not shown) includes a conventional computer hardware and software combination implementing a hypertext browser, display screen with graphics subsystem, and a human-interface device subsystem with associated peripheral hardware, all of which are conventional and represented in FIG. 6 by arrow 677. Operator 678 interacts with the HTTP server over a local, regular network or encrypted network (e.g., with SSL) connection via the hypertext browser, display screen with graphics subsystem, and human-interface device subsystem.

Various particular features of distributed sensor array systems according to various aspects of the present invention may be better understood with reference to the labeled paragraphs or paragraph groups below. In variations where the benefits of these particular features are not required, they may be suitably omitted or modified while retaining the benefits of the various aspects of the invention discussed above. With possible exceptions, structural elements not introduced with a reference numeral are not illustrated in the drawings.

MODULAR CONFIGURATION—Advantageously, a distributed sensor array can have a modular configuration, with its sensor modules deployed and activated as needed in a given situation or threat crisis. The system can initially deploy with no sensor modules at all, if flexibility and minimization of irrelevant sensor resources is paramount. Such a configuration facilitates a rapid response strategy to novel threats. Sensor modules are preferably specialized to detect particular pathogens, chemicals, and types of radiation. Especially on the biological front, there are many possible bacteria, viruses and other pathogens that could be introduced into a reservoir by terrorists or accident. A modular and easily adaptable sensor system is thus highly desirable.

RAPID CUSTOMIZATION—The fact that terrorists have such a wide range of biological, chemical, and radiological agents to choose from means that it is reasonable to plan for a "first strike" with an agent that no existing sensor module is specifically designed to detect. Demand for such a sensor can be expected to skyrocket in the days following such an attack. To deal with such a surge in demand, an operator can inventory modules ready for rapid customization, for example a biological sensor module provided with cantilevers installed but not yet tailored to a particular pathogen. When a biological terrorist attack occurs, the operator can have the agent identified, arrange development of suitable antibodies, apply the antibodies to the cantilevers. With sensor modules already manufactured and ready for customization and rapid deployment, personnel responsible for maintenance of the sensor array system can update it rapidly in the field and obtain appropriate protection.

FSK-MODULATED SENSOR MODULE TRANSMISSION—As an alternative to providing multiple access with CDMA, frequency-division multiple access (FDMA) can be employed with frequency-shift keying (FSK) modulation of individual signals to separate frequency ranges. FSK provides robust bi-directional communications in the presence of noise. The FSK transmitter outputs a signal on one frequency if it is sending a "zero" and another frequency carrier if it is sending a "one." During transmission, one frequency or the other is always present so that there is a continuous signal for the receiver to process and maintain a communications link. The modulation rate of the incoming signal can provide clocking synchronization, reducing the need for a separate clocking signal, especially if phase locked loops (PLLs) are employed. For full-duplex operation, each sensor module transmits modulated information with a different pair of frequencies than the pair on which it receives information. One frequency of each pair represents a "one" and another frequency represents a "zero."

In FSK-modulation variations where the benefits of simultaneous multiple access are not required, all sensor modules can transmit and (in half-duplex operation) receive on a single frequency pair. During a collision caused by two modules transmitting at the same time, one module can be expected to frequently transmit a "one" while the other is transmitting a "zero." The amplitudes of the two signals may be nearly identical as received by the monitoring station, especially if the interfering modules are located at the same distance in the network from the monitoring station. The monitoring station can broadcast a "collision detection" notice in such situations, in which case the sensor modules can execute an exponential backoff algorithm with randomized retry intervals to keep the retries uncorrelated in time.

AM-MODULATED SENSOR MODULE TRANSMISSION—Amplitude modulation (AM) is another FDMA multiple access technique that can be employed. It is simple and inexpensive to implement but suffers from external noise sources such as lightning, EMP, radio transmissions, power line noise and other types of noise. Especially in a single-ended system such as system 100 of FIGS. 1–2, AM modulation may be less desirable than other solutions.

FM-MODULATED SENSOR MODULE TRANSMISSION—Frequency modulation (FM) is a modulation technique that provides some immunity from natural noise sources such as lightning. However, it does not provide the process gain (and consequent immunity to narrowband interference) of a spread-spectrum approach.

OTHER TYPES OF MODULATION IN SENSOR MODULE TRANSMISSION—Phase shift keying (PSK) and quadrature amplitude modulation (QAM) are examples of other types of modulation that can be employed to convey digital baseband information.

CLOCKING SIGNAL—An AC clocking signal can be superimposed on the signal cable to provide a time reference to each sensor module. A sensor module relying on such a clocking signal includes AC coupling circuitry (e.g., circuitry 434 of FIG. 4) and may also include a bandpass filter tuned to the clocking signal. The use of a clocking signal avoids the need for each sensor module to have an on-board oscillator, but a cost vs. performance analysis can be performed to determine trade-offs of external and internal clocking and time references in a given deployment situation.

NETWORKING—Raw information transmission between sensor modules and one or more monitoring stations takes place on a physical layer of simple baseband transmission or a desired type or combination of types of multiple access scheme such as CDMA, FDMA, or TDMA (time-division multiple access). An asynchronous type of TDMA is employed in the Ethernet protocol. If desired for robustness of communications and ease of administration, higher-level networking, e.g., with Ethernet, can be employed as a multiple access scheme and to obtain benefits such as error checking and handshaking. For example, each sensor module can have a unique serial number providing a network address to a monitoring station. Communication over a common signal bus wire is then accomplished using an Ethernet-style collision backoff strategy. Each module transmits the unique serial number and model identification to the host computer. Transmissions are considered to be incomplete until acknowledged by the host computer. If a collision (e.g., simultaneous FSK transmissions from two modules sharing a single signal cable) is detected, or if the monitoring station fails to acknowledge receipt of transmission, an exponential backoff algorithm is employed for retry of the transmission.

RADIOACTIVITY SENSOR MODULE—A number of radioactive toxins are capable of being introduced into the water supply in small quantities that are sufficiently toxic to provide harm to the general population. Specialized sensors for alpha decay, beta decay, and gamma rays can be distributed as needed throughout the array to provide detection and coverage for any radioactive leakage. Such modules could also be useful downstream from nuclear power plants and nuclear storage facilities to monitor any leakage that may occur. For some applications, Geiger counters provide sufficient sensitivity to detect water-borne radioactivity.

CHEMICAL SENSOR MODULES—Chemical modules can search for chemical toxins in the water supply that could threaten the community. Specialized sensors can be designed for individual chemicals. Alternatively, a micro-electro-mechanical system (MEMS) mass spectrometer has been designed and can be adapted for the chemical module that puts a mass spectrometer on a single chip. The mass spectrometer can detect a variety of chemical species with weights from 0 to 50 a.m.u.

Structure of particular interest may be better understood from the abstract of a paper published in Proc. SPIE 4036, 187–193, 2000: "Conventional quadrupole rods have been replaced with a micromachined mass filter made from silicon with Au metallised specially drawn glass fibres of length 30 mm and diameter 0.5 mm. A standard hot filament ion source and both Faraday detection and a channel electron multiplier have been used. The effect of ion focus voltage has also been modelled by SIMION simulation. Conventional electronics were adapted to run at 6 to 8 MHz and mass spectra in the range 0–50 a.m.u. The results indicate a good valley separation between 0, OH, HZO and Ar2' and a best resolution at 10% peak height of 0.9 a.m.u at mass 40 with the multiplier. Application of a static magnetic field transversely to the body of the mass filter is shown to improve resolution howbeit at the expense of ion transmission through the filter." Further information on suitable MEMS structure is presently available at www.microsaic.com.

ANTIBODY-COATED BIOLOGICAL SENSOR MODULES—Modules designed to detect particular biological pathogens can advantageously employ MEMS technology using an oscillating cantilever beam. The cantilever beam is coated with antibodies fixed to the beam and receptive to the pathogen of interest. The frequency of oscillation of the beam decreases when the pathogens stick to the antibodies and are attached to the beam. More information pertinent to cantilever-based sensor technology presently can be found at www.cantion.com.

DETECTOR FILM-COATED BIOLOGICAL SENSOR MODULES—Micro cantilevers can employ a piezoresistive readout as a sensitive biochemical sensor, offering a label detection of molecules. A biochemical reaction at the cantilever surface is monitored as a bending of the cantilever due to a change in the cantilever's surface stress. The change in surface stress is then transformed into a change in the integrated piezoresistor, which is easily monitored by simple instrumentation. Because a very small bending of a cantilever can be measured, this detection method can be very sensitive. With a simple readout technique, this sensor implementation is suitable for decentralized analysis where sample preparation and instrumentation is limited.

In operation, an array of cantilevers is placed in a microliquid handling system, and the cantilevers are coated with a "detector film" that reacts with the biomolecules of interest in a test sample. By coating each cantilever in the array with different "detector films," a multiple of different biomolecules can be detected simultaneously. The change in surface stress on the cantilever surface is related to the change of Gibbs' free energy during the molecular interaction between the biomolecules of interest and the "detector film." Thus the micro cantilevers can therefore be used for detection of a wide variety of molecules like DNA, proteins, antibodies, etc. Micro cantilever-based sensors offer a platform for highly sensitive, label-free molecular recognition on small sample volumes, which could be useful for a point-of-care diagnostic.

WIRELESS TRANSMISSION—In variations where the benefit of transmitting power and data over the same cables that support sensor modules is not required, wireless transmission between sensor modules and a collection point can be employed instead. In one exemplary variation, each sensor module includes an acoustic transducer that can alternately transmit and receive audio signals (e.g., in the 1–20 kHz range, with FSK modulation) through the body of fluid being monitored for contaminants. A collection point can have a corresponding transducer responsive to signals emanating from the various sensor modules of a distributed sensor array. In another variation, each sensor module includes a light emitter and detector, preferably a laser operative in the blue-green spectral peak for light transmission through water. In wireless implementations, supplying power to the sensor modules is a point for consideration. For example, each sensor module can include a battery for self-contained power, but battery life is limited, given non-negligible current draw of the sensor module's electronic circuitry.

PEER-TO-PEER NETWORK TRANSMISSION—Sensor modules of any type, but particularly those transmitting via a lossy wireless link, can benefit in particular situations from a relayed transmission of data to a collection point via a peer-to-peer network of sensor modules. In such a configuration, a given sensor module transmits to a neighboring one, which relays its data on to a sensor module neighboring it that is closer to the collection point than the originating sensor module, and so on.

OTHER NETWORK TOPOLOGIES—Other type of network topology that can be employed include a star-based hierarchical network transmission system using network switches, and full-mesh transmissions systems. The latter may be a subset of the peer-to-peer network type.

ARRAY MAINTENANCE WITH AUTONOMOUS VEHICLE(S)—In an advantageous variation, drone vehicles that operate completely autonomously or under at least partial remote human control assist in or completely undertake particular mechanical operations. Such operations can include servicing, maintaining, deploying and retrieving sensors on an array of cables according to various aspects of the invention. For example, a remotely operated vehicle (ROV) can include a robotic arm capable of actuating a clasping mechanism, vampire clamp, or cable tie (or a combination of some or all of those actuations) in situ at a desired location along a sensor array. Such a vehicle could plug into suitable portions of the array for primary or supplemental power. It could use the cables of the array for structural support, even relying on them to move in spider fashion along the array to different sensor modules. The use of unmanned vehicles could in some implementations greatly reduce cost and possible personnel risk that might otherwise be associated with sensor array maintenance.

The detailed description of preferred exemplary embodiments above mentions certain patents and publicly accessible documents. The detailed description portions of all the aforementioned patents, and the contents of all the aforementioned publicly accessible documents, are hereby incorporated herein by reference. The detailed description portions of all U.S. patents and patent applications incorporated by reference into these listed patents or applications are also specifically incorporated herein by reference.

PUBLIC NOTICE REGARDING THE SCOPE OF THE INVENTION AND CLAIMS

The inventors consider various elements of the aspects and methods recited in the claims filed with the application as advantageous, perhaps even critical to certain implementations of the invention. However, the inventors regard no particular element as being "essential," except as set forth expressly in any particular claim. For example, information-transmissive cables of the electrical type are not "essential" to an invention claimed without limitations as to a particular type of information-transmissive cable.

While the invention has been described in terms of preferred embodiments and generally associated methods, the inventors contemplate that alterations and permutations of the preferred embodiments and methods will become apparent to those skilled in the art upon a reading of the specification and a study of the drawings. For example, the rationale for monitoring need not be limited to preventing possible terrorist attacks against reservoirs, but also can be directed to environmental compliance monitoring, pollution control, and aquaculture development. In one case, a corporation might install a sensor array system according to various aspects of the invention downstream from its discharge locations to verify to municipalities that it complies with federal clean water statutes. In another case, fish farmers might monitor for the presence of pathogens near their fish farms and take evasive measures to prevent harm to their fish stocks.

Additional structure can be included, or additional processes performed, while still practicing various aspects of the invention claimed without reference to such structure or processes. For example, decontamination subsystems including oil-absorbing devices can also include retractable coverings for such devices (to avoid water exposure until decontamination is needed) read on claims not specifically reciting such coverings.

Accordingly, neither the above description of preferred exemplary embodiments nor the abstract defines or constrains the invention. Rather, the issued claims variously define the invention. Each variation of the invention is limited only by the recited limitations of its respective claim, and equivalents thereof, without limitation by other terms not present in the claim. For example, a claim that merely calls for a system comprising a sensor, an integrated power supply, and a telemetry system reads on systems having just one sensor, multiple sensors of the same type, and multiple sensors of different types.

In addition, aspects of the invention are particularly pointed out in the claims using terminology that the inventors regard as having its broadest reasonable interpretation; the more specific interpretations of 35 U.S.C. § 112(6) are only intended in those instances where the terms "means" or "steps" are actually recited. For example, the term "strand" as used herein refers to any long, thin, filament-type structure forming part of a cable, and is not limited to fiber strands of ropes or any other particular form of cable component. As another example, the terminology "fixed in place" and variations thereof indicate that a structure is immobile and fixed (e.g., connected by an anchor) at a particular location. It does not preclude the structure having some swaying or other non-cumulative motion relative to the location in which it is "fixed in place."

The words "comprising," "including," and "having" are intended as open-ended terminology, with the same meaning as if the phrase "at least" were appended after each instance thereof. A clause using the term "whereby" merely states the result of the limitations in any claim in which it may appear and does not set forth an additional limitation therein. Both in the claims and in the description above, the conjunction "or" between alternative elements means "and/or," and thus does not imply that the elements are mutually exclusive unless context or a specific statement indicates otherwise.

What is claimed is:

1. A method for monitoring fluid impurity levels, comprising:
   (a) fixing a network of cables in place within a fluid;
   (b) supporting a plurality of first sensors sensitive to a first fluid impurity at different places on the cable network;
   (c) supporting a plurality of second sensors sensitive to a second fluid impurity, different from the first fluid impurity, at different places on the cable network; and
   (d) transmitting to a collection point data representative of the level of first and second fluid impurities in the fluid.

2. The method of claim 1 further comprising deploying a plurality of oil-absorbing devices proximate to the cable network.

3. The method of claim 1 wherein the second sensors are located at different places on the cable network than the first sensors and the first and second sensors are located proximate to different junctions of pairs of the cables.

4. The method of claim 1 wherein the cable network comprises a first set of cables placed parallel to each other substantially in a common plane and a second set of cables placed perpendicular to the first set of cables and substantially in the same plane.

5. The method of claim 1 further comprising, after parts (a)–(d), supporting a plurality of third sensors sensitive to a third fluid impurity different from the first and second fluid impurities, at different places on the cable network, and thereafter transmitting to the collection point data representative of the level of first, second, and third fluid impurities.

6. The method of claim 1 further comprising, after parts (a)–(d), replacing the first sensors with a plurality of third sensors sensitive to a third fluid impurity different from the first and second fluid impurities, at different places on the cable network, and thereafter transmitting to the collection point data representative of the level of second and third fluid impurities.

7. The method of claim 1 wherein supporting the pluralities of sensors includes supporting a plurality of rows or columns of sensors.

8. The method of claim 1 wherein transmitting data includes transmitting electrical signals via the cables.

9. The method of claim 8 further comprising transmitting a plurality of modulated electrical signals from the collection point.

10. The method of claim 9 wherein the modulated electrical signals are transmitted with CDMA modulation, wherein each one of the plurality of signals is modulated with a different spreading code.

11. The method of claim 8 wherein supporting the sensors includes supporting a plurality of sensor modules that each house one of the sensors.

12. The method of claim 11 wherein transmitting electrical signals includes, for each one of the sensors:
 (a) transmitting analog data proportional to a level of fluid impurity from the sensor to the sensor module housing it; and
 (b) transmitting modulated digital data based on the analog data from the sensor module to the collection point.

13. The method of claim 11 further comprising, before part (d), supplying electrical power to the sensor modules as a DC offset superimposed on the transmitted electrical signals.

14. The method of claim 11 further comprising, after part (a), electrically connecting each one of the sensor modules to at least one of the cables via a clamp that includes an insulation-piercing probe placed in direct contact with an electrical conductor of the cable.

15. A fluid impurity monitoring system comprising:
 (a) a network of cables fixed in place within a fluid;
 (b) a plurality of first sensors sensitive to a first fluid impurity supported at different places on the cable network;
 (c) a plurality of second sensors sensitive to a second fluid impurity, different from the first fluid impurity, supported at different places on the cable network; and
 (d) a collection point responsive to data, transmitted from the sensors, that is representative of the level of first and second fluid impurities in the fluid;
whereby the level of different fluid impurities at different places within the fluid can be collected and monitored.

16. The system of claim 15 further comprising a plurality of oil-absorbing devices proximate to the cable network.

17. The system of claim 15 wherein the second sensors are located at different places on the cable network than the first sensors and the first and second sensors are located proximate to different junctions of pairs of the cables.

18. The system of claim 15 wherein the cable network comprises a first set of cables placed parallel to each other substantially in a common plane and a second set of cables placed perpendicular to the first set of cables and substantially in the same plane.

19. The system of claim 15 further comprising a plurality of third sensors, sensitive to a third fluid impurity different from the first and second fluid impurities, supported at different places on the cable network; wherein the collection point is further responsive to data representative of the level of first, second, and third fluid impurities.

20. The system of claim 15 wherein the pluralities of sensors include a plurality of rows or columns of sensors.

21. The system of claim 15 wherein the collection point is responsive to data that is electrically transmitted via the cables.

22. The system of claim 21 wherein the collection point is responsive to modulated data transmitted as a plurality of signals from a plurality of the sensors multiplexed onto ones of the cables shared by multiple ones of the sensors.

23. The system of claim 22 wherein the data is multiplexed with CDMA and each one of the plurality of signals is modulated with a different spreading code.

24. The system of claim 21 further comprising a plurality of sensor modules that each house one of the sensors, wherein, for each one of the sensor modules:
 (a) the sensor module is responsive to analog data, proportional to a level of fluid impurity, from the sensor it houses; and
 (b) the collection point is responsive to modulated digital data, based on the analog data from the sensor, transmitted from the sensor module.

25. The system of claim 24 further comprising a source of electrical power, coupled to the sensor modules via the same cables employed for transmission of the electrical signals.

26. The system of claim 24 wherein each one of the sensor modules includes a clamp that includes an insulation-piercing probe, whereby the probe can be placed in direct contact with an electrical conductor of one of the cables and the sensor modules can electrically connect to the cable via the probe.

27. A method for monitoring fluid impurity levels, comprising:
 (a) fixing a network of electrically conductive cables in place within a fluid substantially in a common plane, wherein some cables of the network are oriented substantially parallel to each other and intersect other cables of the network;
 (b) supporting a plurality of sensors on the network proximate to different junctions of pairs of the cables; and
 (c) transmitting, to a collection point via a separate electrical circuit for each one of the sensors, data representative of the degree of fluid impurities in the fluid, wherein the electrical circuit for each sensor includes a series connection of the pair of cables that intersect proximate to where the sensor is supported on the network.

28. The method of claim 27 wherein intersecting cables of the network are oriented substantially perpendicular to each other.

29. The method of claim 28 wherein: (a) some cables of the network are substantially vertical and the other cables of the network are substantially horizontal, and (b) the sensors are arranged in a regular array.

30. The method of claim 27 wherein supporting a plurality of sensors includes:
 (a) supporting a plurality of first sensors sensitive to a first fluid impurity at different places on the cable network; and
 (b) supporting a plurality of second sensors sensitive to a second fluid impurity, different from the first fluid impurity, at different places on the cable network.

31. The method of claim 30 wherein the second sensors are located at different places on the cable network than the first sensors.

32. The method of claim 27 wherein supporting the sensors includes supporting a plurality of sensor modules that each house one of the sensors.

33. The method of claim 32 wherein transmitting electrical signals includes, for each one of the sensors:

(a) transmitting analog data proportional to a level of fluid impurity from the sensor to a sensor module housing the sensor; and (b) transmitting modulated digital data based on the analog data from the sensor module to the collection point.

34. The method of claim 32 further comprising, before part (c), supplying electrical power to the sensor modules as a DC offset superimposed on the transmitted electrical signals.

35. The method of claim 32 further comprising, after part (a), electrically connecting each one of the sensor modules to at least one of the cables via a clamp that includes an insulation-piercing probe placed in direct contact with an electrical conductor of the cable.

36. The method of claim 27 wherein some cables of the network are substantially vertical and the other cables of the network are substantially horizontal.

37. The method of claim 36 further comprising, for each one of the sensor modules, employing one of the vertical cables as a ground connection in the circuit.

38. A fluid impurity monitoring system comprising:

(a) a network of electrically conductive cables fixed in place within a fluid substantially in a common plane, wherein some cables of the network are oriented substantially parallel to each other and intersect other cables of the network;

(b) a plurality of sensors supported on the network proximate to different junctions of pairs of the cables; and (c) a collection point responsive to data, transmitted via a separate electrical circuit for each one of the sensors, that is representative of the degree of fluid impurities in the fluid, wherein the electrical circuit for each sensor includes a series connection of the pair of cables that intersect proximate to where the sensor is supported on the network;

whereby the level of different fluid impurities at different places within the fluid can be collected and monitored.

39. The system of claim 38 wherein the sensors are arranged in a regular array including a plurality of rows and columns of sensors.

40. The system of claim 38 wherein the sensors are located proximate to different junctions of pairs of the cables.

41. The system of claim 38 wherein the plurality of sensors includes:

(a) a plurality of first sensors sensitive to a first fluid impurity and supported at different places on the cable network; and (b) a plurality of second sensors sensitive to a second fluid impurity, different from the first fluid impurity, supported at different places on the cable network.

42. The system of claim 38 wherein the collection point is responsive to modulated data transmitted as a plurality of signals from a plurality of the sensors multiplexed onto ones of the cables shared by multiple ones of the sensors.

43. The system of claim 42 wherein the data is multiplexed with CDMA and each one of the plurality of signals is modulated with a different spreading code.

44. The system of claim 38 further comprising a plurality of sensor modules that each house one of the sensors, wherein, for each one of the sensor modules:

(a) the sensor module is responsive to analog data, proportional to a level of fluid impurity, from the sensor it houses; and (b) the collection point is responsive to modulated digital data, based on the analog data from the sensor, transmitted from the sensor module.

45. The system of claim 44 further comprising a source of electrical power, coupled to the sensor modules via the same cables employed for transmission of the electrical signals.

46. The system of claim 44 wherein each one of the sensor modules includes a clamp that includes an insulation-piercing probe, whereby the probe can be placed in direct contact with an electrical conductor of one of the cables and the sensor modules can electrically connect to the cable via the probe.

47. A fluid impurity monitoring system comprising:

(a) a network of electrically conductive cables fixed in place within a fluid;

(b) sensor means, supported at different places on the cable network, for sensing the level of different types of fluid impurities at different locations in the fluid; and (c) means for electrically transmitting, via series connections of the cables, and for collecting data representative of the impurity levels.

\* \* \* \* \*